United States Patent [19]

Young et al.

[11] Patent Number: 5,429,588

[45] Date of Patent: Jul. 4, 1995

[54] ANKLE FOOT ORTHOSES KNOWN AS LOWER LEG WALKERS

[75] Inventors: David E. Young, Watlington; Colin A. Young, Abingdon, both of England

[73] Assignee: Innovative Care Ltd., Oxforshire, England

[21] Appl. No.: 197,147

[22] Filed: Feb. 16, 1994

[30] Foreign Application Priority Data

Feb. 17, 1993 [GB] United Kingdom ............. 9303116

[51] Int. Cl.⁶ ........................................ A61F 5/00
[52] U.S. Cl. ................................ 602/27; 602/10; 36/28
[58] Field of Search ................ 602/10, 23, 27; 36/11.5, 28, 110

[56] References Cited

U.S. PATENT DOCUMENTS

| | | | |
|---|---|---|---|
| 1,994,681 | 3/1935 | Blumenfeld | 36/28 X |
| 2,760,279 | 8/1956 | Jones et al. | 36/11.5 |
| 2,981,011 | 4/1961 | Lombardo | 36/28 X |
| 3,890,725 | 6/1975 | Lea et al. | 36/11.5 |
| 4,378,793 | 4/1983 | Mauldin et al. | 602/27 |
| 4,414,759 | 11/1983 | Morgan et al. | 36/110 X |
| 4,414,965 | 11/1983 | Mauldin et al. | |
| 4,425,721 | 1/1984 | Spronken | 36/110 X |
| 4,572,169 | 2/1986 | Mauldin et al. | 602/27 |
| 4,771,768 | 9/1988 | Crispin | 602/27 X |
| 4,919,118 | 4/1990 | Morris | |
| 4,974,583 | 12/1990 | Freitas | 602/27 X |
| 5,078,128 | 1/1992 | Grim et al. | 602/23 |
| 5,088,481 | 2/1992 | Darby | 602/23 |
| 5,092,321 | 3/1992 | Spademan | 602/27 |
| 5,176,623 | 1/1993 | Stetman et al. | 602/27 |
| 5,183,036 | 2/1993 | Spademan | 602/27 X |
| 5,250,021 | 10/1993 | Chang | 602/27 |

*Primary Examiner*—Linda C. M. Dvorak
*Attorney, Agent, or Firm*—Tilton Fallon Lungmus

[57] ABSTRACT

A Lower Leg Walker for the treatment of ankle fractures and a variety of other injuries to the foot and ankle, has a foot platform base comprising a rigid chassis of more or less parallelepiped shape. The chassis is substantially a plurality of ribs disposed at right angles, forming a grid and is over-moulded with resilient materials forming a shoe shape. The foot platform base supports and accommodates the human foot and has a distinctive, low, double rocker profile on its underside. The lower leg walker is provided with attachment hinges for securing a pair of upright side-members to the foot platform base and these are covered with hook and loop attachment material which releasably secures them to a wrap which is lined with terry material and encloses the foot, ankle and lower leg. The device is secured to the patient with a series of straps.

10 Claims, 7 Drawing Sheets

ANKLE FOOT ORTHOSES KNOWN AS LOWER LEG WALKERS

BACKGROUND OF THE PRESENT INVENTION

Lower leg walkers are a class of off-the-shelf ankle foot orthosis developed in the USA early in the nineteen-eighties. An ankle foot orthosis is a device fitted to the ankle and foot to provide at least a partial substitute for some of the functions of the ankle joint. In the case of lower leg walkers, the main application is in assisting the ligamentous structures of the joint to resist inversion and eversion and in some cases to immobilize the joint.

Lower leg walkers have a foot platform and extend proximally about the ankle and lower leg, normally ending a short distance below the knee. Their structural antecedents are below knee plaster casts and traditional orthoses, such as those used for the victims of poliomyelitis and cerebral palsy. The main aim of those orthoses is to help patients with walking difficulties to walk more easily. It remains common practice to build orthoses which combine a double acting or other ankle hinge with a foot platform, often one having a rocker sole, in order to limit ankle travel and facilitate ambulation.

Indications for lower leg walkers have been extended by orthopaedic surgeons and orthotists. In the U.S.A. most seem to agree that they are indicated in non-displaced ankle fractures, march fractures, severe sprains and post-operative use following certain ankle ligament reconstructive procedures.

Polakoff et al, *Orthopedics* November 1984 Vol 7/No 11: 1712-1715, trialling an early lower leg walker, stated that " . . . the treatment of stable ankle fractures with an ankle foot orthosis (of the lower leg walker type) can significantly decrease the time until clinical union, and the complication of "fracture disease" associated with plaster immobilisation. Specifically, post-treatment tenderness, edema, and atrophy were diminished, while range of motion was maintained." They go on to say future investigations should explore other types of ankle injuries and surgically stabilized conditions using orthoses of this type.

Only a small number of workers has actually published in this field. In 1989, Neumann et al reported significantly less muscle wastage and joint stiffness in healthy volunteers wearing lower leg walkers than in a comparable group in short leg casts. They also refer to 48 cases of injured lower limbs treated in lower leg walkers including foot, lower tibia and fibula injuries as well as ankles. A somewhat different orthosis was investigated earlier by Stover and York whose 164 cases included numerous fractures of tibia and fibula including 9 cases of compound fractures of tibia and fibula.

There is a dearth of good comparative studies on the efficacy of lower leg walkers versus standard treatments in any condition other than ankle fractures. However, in 1993, Klenerman's group in Liverpool, U.K. completed a study of early mobilization versus plaster immobilization following operative repair of ruptured Achilles tendon. They used hinged lower leg walkers designed by the present authors. Scanning techniques were used to assess rates of healing of the tendon with each method and objective assessment of rehabilitation was also employed. The results were favorable to the lower leg walker regime.

Nowadays, it is generally accepted that mobilization soon after injury produces benefits. Treatment is generally directed to shortened rehabilitation periods and benefits include a quicker return to function and better ultimate outcome. There is less loss of muscle bulk, oedema subsides more rapidly and diminution in proprioception is minimized. In stable ankle fractures, severe sprains and certain foot fractures, most of the benefits may be realized within a regime utilising a lower leg walker, without hinges, in which the patient walks according to a protocol laid down by the carer. On the other hand, more demanding protocols may be employed when a hinged walker is used. As an ever widening group of patients is being treated with this type of orthosis, it is clear that the greatest benefit from any invention relating to lower leg walkers will be gained if it can be applied to both hinged and non-hinged types.

So far as we have been able to ascertain, there is little objective evidence to demonstrate either the efficacy or safety of 'conventional' lower leg walkers in treating any fracture of the tibia or fibula. Only the recent Klenerman study applying to walkers designed by the present authors suggests that they have a definite, safe place in the post-operative treatment of surgical repairs to ruptures of the Achilles tendon. Nevertheless, it is known that large numbers of these devices are used in the treatment of both these categories of injury.

Only a small number of lower leg walkers is used outside the USA and Canada. However, the concept has now been established long enough to overcome the conservatism of surgeons and orthotists in Europe. Even so, it seems unlikely that the acceptance in Europe will reach the levels seen in North America before the end of the century.

DESCRIPTION OF THE PRIOR ART

The first conventional lower leg walkers came on to the U.S. market in the early nineteen-eighties. These designs did not have hinges at the ankle joint and were generally intended to prevent motion at the ankle. They featured a foot platform base and a pair of upright side-members disposed medially and laterally. They were direct substitutes for short leg walking casts and they became known as 'Fixed' lower leg walkers whereas designs which feature hinges have been dubbed 'Range of motion'. 'Hinged' or 'Variable motion' lower leg walkers.

In the early, fixed, designs the foot platform base was made of wood, as disclosed in U.S. Pat. No. 4,378,793 granted to Maudlin and Jones on Apr. 5th, 1983. Another patent, U.S. Pat. No. 4,414,965 was granted to the same authors on Nov. 15th, 1983, in respect of a Brace for Tibial Fractures. This also discloses a wooden base secured to upright side-members by means of threaded fasteners. The use of a wood foot platform is indicative of the need for a substantially rigid base at the core of a lower leg walker. This is necessary to limit motion of the bones of the ankle and foot and their related ligamentous structures which may be injured.

In U.S. Pat. No. 4,572,169 granted to Maudlin and Jones on Feb. 25th, 1986, there is described a Removable Leg Brace. In this patent the authors admit that the wooden base-to-upright attachment, described in their earlier patents, loosens with use. This 1986 patent to Maudlin and Jones discloses a rigid moulded foot piece with broad upright extensions which cover the ankles during use. The moulded foot piece has a bottom wall, a side-wall and ribs disposed longitudinally and transversely which extend upwardly from the bottom wall to a plane lying beneath the upper edge of the side-wall. In this device there was no equivalent to the 'upper' of a shoe and the sole was a tread strip bonded to the underside of the bottom wall. A plastics blank covered the upper surface of the foot platform and a soft insole supported the foot. This walker was of a type which has come to be known by those skilled in the art as a 'mid-stance walker' because the underside of the foot platform base has a flat mid-section. This allows the wearer to stand for extended periods without fatigue. There is little doubt that this foot platform would provide the necessary rigidity, however, the thin tread strip under the bottom wall would provide little attenuation of shock loads transmitted to the injured bone or joint at the initial part of the gait cycle known as 'heel strike'.

Numerous other lower leg walkers have since employed a moulded foot platform base with an entire bottom wall and internal ribs. The present authors designed such a foot platform base in 1984 and it was sold commercially as a component within both fixed and hinged lower leg walkers until early 1993.

Another example of a this general type is found in the CAM Walker sold by Messrs United States Manufacturing Company and Messrs Zinco, both of Pasadena, Calif., USA. This product is similar to the device described in U.S. Pat. No. 4,771,768 granted to George E. Crispin on Sep. 20th, 1988, which describes a Controlled Motion Ankle Fracture Walker. This device has a rocker sole which, the preamble to the patent concedes, was well known at the time of filing. It goes on to describe upright side-members controlled by a single pivot axis, double acting, ankle hinge of a type and design which we have established was invented by Louise Becker in 1963 and which has been used in vast numbers in ankle foot orthoses all over the world since then. The original maker and seller of this double-acting ankle hinge is Becker Orthopedic of Troy, Mich., USA and it has appeared in their catalogue since at least the mid nineteen-sixties. Such double-acting ankle hinges have also been made and sold for more than fifteen years by Otto Bock GmbH of Düderstadt, Germany. Such adjustable ankle hinges have a first adjustable abutment screw and a first rigid stop located anteriorly, with respect to the pivot axis and a second adjustable abutment screw and a second rigid stop, located posteriorly with respect to the pivot axis. From this description it will be clear that access to the first and second adjustable abutment screws is from above.

The lower leg walkers hereinbefore described have foot platforms of adequate rigidity but thin tread soles of limited resilience. Such soles also have limited wear life and skidding is a possibility if the patient strikes the foot platform onto the ground at an angle which allows a non-treaded area to make contact.

Most fixed lower leg walkers have upright side-members attached directly to the foot platform base. In some cases, upright side-members are secured by over-moulding and in others by riveting or threaded fasteners. Upright side-members are generally made of metal or plastics. Typically, metal upright side-members extend under the foot platform base and up, alongside the lateral and medial aspects of the ankle, ending a little below the knee. In lower leg walkers which have plastics upright side-members, these are often attached via clip or locking means into side pockets or other adapter means incorporated directly into side-portions or side-extensions in the foot platform base. An example of this type is the Equalizer model fixed lower leg walker supplied by Centec Inc., Westlake Village, Calif., USA.

In hinged lower leg walkers, attachment means between the foot platform base and the upright side-members are often also part of or integral with, the hinging means. Upright side-members are subjected to significant torque, as well as cyclic bending loads during the gait cycle and many failures of lower leg walkers are due to material fatigue resulting from these and other repeated stress reversals.

Some lower leg walkers have plastics paddles or shells attached to the upright side-members to provide partial encirclement of the lower leg. In some examples these are attached removably and in others, non-removably. A removable paddle type was designed by the present authors and made by Protectair Limited, Abingdon, Oxfordshire, U.K. In the U.S.A. this device was sold by Protectair Incorporated of Downers Grove, Ill.

Other models do not have paddles or shells and instead employ upright side-members incorporating strap mounting means. An example of this type has been sold by Donjoy Inc., Carlsbad, Calif., USA. Another alternative to paddles and shells is the use of upright side-members covered with loop and pile closure fabrics of the type known commercially as Velcro®, which perform in this context as mounting or securing means for the fixing straps. Examples of this type have been sold by Medical Technology Inc. of Grand Prairie, Tex., USA and Messrs United States Manufacturing Company and Zinco Industries, both of Pasadena, Calif., USA.

In both hinged and fixed lower leg walker types, the foot, ankle and lower leg are all generally enclosed in a shaped wrap made of foamed plastics with an outer fabrics facing. Furthermore, it is normal in conventional lower leg walkers to secure the foot, ankle and lower leg within the device by means of a series of straps made of hook and loop fabric such as sold under the trademark Velcro®. Typically, there are three of these straps for the lower leg, one for the ankle and two for the foot.

Some lower leg walkers have employed foot base platforms made by vacuum forming or plastics injection moulding which incorporated rigid upward extensions of a peripheral side-wall of the foot platform base around the foot and heel. This allows the straps to be tightened without compressing the foot and therefore avoids pain if the foot is tender. However, this arrangement also precludes any possibility of the device conforming to the foot. Conformability could be useful if the foot was not involved in the injury and secure direct capture of it was desirable.

One model introduced by the American firm Orthopedic Technology Inc. of San Leandro, Calif., USA, during the mid nineteen-eighties made extensive use of vacuum forming. A large component combined the functions of the foot platform base, upright side-members and paddles also extended right around the posterior aspect of the lower leg. Although we have not handled a hinged version of this device, such a design is disclosed in U.S. Pat. No. 4,919,118 granted to John C. Morris on 24th Apr. 1990. Another manufacturer, Air-Cast of Summit, N.J., USA, has extended the vacuum formed coverall shell approach to providing linings filled with air or gel. We have not seen a hinged version of this device.

It is apparent that patients spend much more time standing still in a lower leg walker than they do actively ambulating. Whilst they require a platform which allows them to stand in a stable and comfortable manner, conventional mid-stance walkers are often more difficult to walk on than rocker types. Conversely, patients often find rocker-sole walkers make them feel unstable during walking since there is no mid-stance 'stop' point. Some patients also find rocker-soled walkers tiring to stand in for long periods for the same reason. This is because sensory nerve endings in both the anterior tibialis muscle and the gastrocnemius are stimulated all the time, producing a more or less continuous motor response leading to fatigue.

Many lower leg walker designs incorporate a simple rocker sole into the underside of the base. This is often much narrower than the width of the foot platform and also often narrower than the base of a normal shoe. A narrowed base reduces stability and furthermore, a marked rocker profile imparts considerable height to a walker which also reduces stability. It is uncommon to find a walker which has a height similar to that likely to be found in the footwear worn on the contra-lateral foot yet Hamzeh, Bowker and Rowley; Clinical Biomechanics 1988:3: 74–78, have shown that " . . . addition of the rocker leads to an increase in energy cost (of walking) of 45% . . . ". Although this study was of below knee walking casts, such a construct and a lower leg walker are precise analogues. This study goes on to show that there is a similar penalty when height raise is introduced, even without a rocker, and that the penalty in terms of energy cost for inclusion of either of these two features is much greater than that for increased weight. It may be concluded that neither the inclusion of a single rocker nor the provision of high flat mid-section in a walker is beneficial to the patient.

For obvious safety reasons lower leg walkers need a non-slip walking tread. All the designs we have encountered, including our own earlier designs, have relied upon an entire or continuous under surface or bottom wall of the base to provide mounting means for a bonded tread strip. With this arrangement, there is always the risk of partial or complete tread detachment. This could lead to a patient, whose capacity to recover balance is already impaired, tripping or falling. In addition, thin tread-strips have limited resilience and they do not attenuate the shock of heel strike very well. Worn tread-strips offer virtually no attenuation of shock on heel strike. Patients also report occasional instances of skidding in narrow tread walkers when a part of the base, not covered by tread, strikes the ground and is subjected to a transient load.

In prior art walkers we have found designs with no peripheral wall or which have a rigid peripheral wall (structurally equivalent to the upper of a shoe) extending around the foot. The former type allows the foot to be compressed by retaining straps and use of this design has declined in recent years. However, it did have the advantage of precluding movement of the foot within the walker. The rigid peripheral wall type prevents the foot from being compressed from the side (although it is often compressed from above by straps passing over the instep). The rigid peripheral wall type does not conform at all and this limits good capture of the foot. In some instances the foot can move within the constraints of the wall, wraps and straps. This defeats the object of treatment and may put the patient at risk.

None of the prior art walkers we encountered offered a inner facing-fabric for contact with the skin which had any marked absorbency, although some uptake of moisture through facings into the open cell body material of the wrap did occur. Some wraps have no inner facing at all, some are made of the same brushed nylon material as the outer facing and some are made of tricot or scrim.

SUMMARY OF THE PRESENT INVENTION

The present invention is directed towards improvements to lower leg walkers in order to improve significantly the conservative management and rehabilitation of ankle fractures, certain types of foot fracture, severe sprains and post-operative management of surgical repair following rupture of the Achilles tendon. The lower leg walker of this invention provides a low, resilient, moulded foot platform base which has a strong, rigid, internal chassis allowing numerous benefits to accrue during the rehabilitation process which are not available with prior art walkers. The lower leg walker of the present invention has upright side-members which may be provided with either rigid or hinged attachment means to the foot platform base and has wrap means with moisture absorbing linings. Improvement in rehabilitation may be gained through the novel features of the present invention in a wider range of conditions and with better patient compliance and lower energy cost than with prior art devices.

We studied lower leg walkers during their use on patients noting, in particular, factors which affected compliance.

There is a requirement for a lower leg walker which will allow the patient to stand comfortably for extended periods and which has a sole no thicker than the height of a typical shoe likely to be worn on the contra lateral foot in order to minimize energy cost.

There is a requirement for a lower leg walker which has a resilient foot platform which cannot detach or skid.

There is a requirement for a variant which has hinges which may be adjusted from a posterior direction with the device in situ. Prior art walkers with hinges are adjusted from above or towards the ankle. This is not easy in the case of the former and can involve directing a pointed implement towards the injured ankle or lower limb in the case of the latter.

There is a requirement for a lower leg walker which has flexible uppers or side-walls to capture the patient's foot in a conformable manner, limiting its ability to migrate within the device whilst ensuring that compression from retaining straps is evenly distributed and therefore kept to relatively low load levels at all contact points.

There is a requirement for a lower leg walker with wrap facings which are comfortable and will absorb sweat.

The present invention fulfils the foregoing requirements to provide an improved ankle foot orthosis which is useful in the medical treatment of conditions of the foot and ankle where a sound rationale exists for treatment by lower leg walkers.

Briefly, the lower leg walker of the invention includes a substantially rigid base or chassis which is over-moulded with a resilient material so as to provide a strong composite foot base platform with an integral tread and flexible side-walls or uppers. The integral tread formed in the over-mould comprises a first rocker profile which extends under the forefoot and a second rocker profile which extends under the hindfoot. The zone between the rocker profiles under the midfoot area is relieved, in marked contradistinction to prior art rocker designs, which are built up in this area to their maximum thickness.

Together, the first and second rocker profiles allow the foot base platform to rest at mid-stance across two bridging zones which are substantially tangential to the plane of the ground. The flexible upper extends upwards from the foot platform base, arising near the metatarsal margins, rising around the periphery to reach a maximum height around the calcaneal area. Rigid upwards extensions from the chassis are adapted to receive fixing means for medial and lateral upright side-members. The upright side-members each have an adhesive hook strip, applied over the inner aspect and an adhesive loop strip applied over the outer aspect. A wrap for enclosing the foot, ankle and lower leg is cut from open cell foamed plastics sheet and has terry material bonded to the inner surface. Brushed nylon material is bonded to the outer surface and this is attachable to hook material. Strips of hook material are provided by means of which the wrap is secured to itself and around the patient's limb. A set of straps is provided for securing the device to the foot, ankle and lower leg of the patient.

A distinctive feature of the present invention is that the foot platform assembly comprises two principal components. The first component is a rigid, chassis of very low height, having the shape of a modified right-prism or parallelepiped and which is essentially a perforate, open, grid-like structure which does not have an entire or imperforate bottom wall. The second component is an over-mould which almost completely encloses the chassis. This over-mould is durable, resilient and in those parts of it which have a thin section, flexible. The resultant composite foot platform base structure has great strength and inherent rigidity as well as overall resilience by virtue of its novel design and the physical properties of the materials from which it is made. The composite foot platform is also very low in height. This form of construction is in marked contradistinction to prior art devices. The rigid chassis has upward extensions which arise from below the malleolar area on each side and which are adapted to receive attachment means for hinging means or to provide direct mounting means for upright side-members.

Another distinctive feature is that the over-mould provides an integral tread which has a complex longitudinal profile in which a first rocker profile extends about the fore part of the foot and a second rocker profile which extends about the hind part of foot. When the lowest points of these two profiles, which are transverse corrugations, are in contact with the ground, they act as bridging zones. When the lower leg walker rests on these ground contact lines, it is in stable equilibrium and the wearer is in the mid-stance position. Because the tread is an integral part of the over-mould, there is no risk of detachment or skidding and it has an almost unlimited life in normal clinical use. Furthermore, because the resilient over-mould completely covers those parts of the foot platform base which come into contact with the ground and all those parts which come into direct contact with the patient, the structure offers enhanced shock attenuation throughout the gait cycle. Furthermore, the low overall height of the foot platform base and the omission of a high mid-foot rocker, together with the marked roll-in profile at the heel and roll-off profile and flexibility at the toe, contribute to normalizing the gait pattern and minimizing the energy cost of walking.

Another distinctive feature is that the over-mould provides flexible side-walls or uppers extending upwards and substantially around the periphery of the moulded base, including around the calcaneal area, so that the foot may be accommodated and secured with greater comfort and conformance than in prior art lower leg walkers.

Yet another distinctive feature resides in the provision of a wrap lined with an inner facing of terry material. This is significantly more absorbent and comfortable than the brushed nylon or nylon scrim of prior art walkers and consequently has the potential for significantly improving patient compliance.

Two most preferred embodiments will now be described. The first most preferred embodiment is a hinged lower leg walker according to the present invention. The second most preferred embodiment is a fixed version of a lower leg walker according to the present invention. Both these embodiments will now be described in greater detail by way of reference to the accompanying drawings.

FIGS. 1 to 9, refer to the first most preferred embodiment in which:

FIGS. 10 and 11, relate to the second, most preferred embodiment of a lower leg walker according to the present invention which is substantially identical in all respects to the first most preferred embodiment described with reference to FIGS. 1 to 9, except that no hinging means are provided and in which:

Referring to FIGS. 1 to 8 and 10 and 11, of the drawings, certain directions are referenced to the position of components or movements of the human body. An outline of the human lower leg, including the ankle and foot, is designated 1.

In FIGS. 1–6 of the drawings, the numeral 10, generally designates a lower leg walker that includes a foot platform base 12, comprising a chassis 14, substantially covered by an over-mould 16, which extends upwards into a flexible upper 18, peripherally, above and forming a sole 20, below. The sole 20, has a first rocker profile 22, at the front end and a second rocker profile 24, at the rear or heel end. The chassis 14, has upward extensions in the malleolar area which are exposed at 26 and 27 and are adapted to receive upright side-members 28 and 29.

The elements of foot platform base 12, are intimately associated by virtue of chassis 14, which is formed by injection moulding a high strength, substantially rigid, composite material formed of a plastics or resin substrate having a suitable reinforcement phase such as glass- or carbon-fibre, being substantially covered by the substance of over-mould 16. Over-mould 16, is a plastics system, such as a urethane, having physical characteristics of durability, resilience, flexibility in thinner sections and good bonding properties. It is formed by a low pressure moulding process. Upright side-members 28 and 29, are preferably fabricated in hard metal, such as stainless steel, having a rectangular cross-sectional area.

Figure 3:
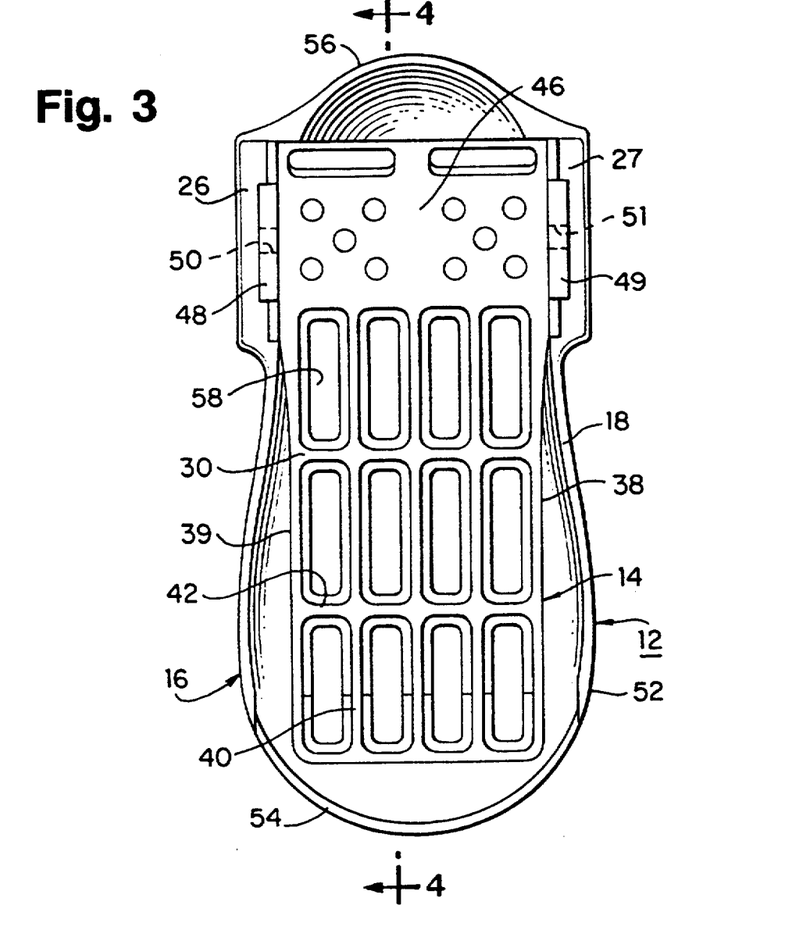
FIG. 3, is a plan section view of the moulded platform base through the line B–B1 in FIG. 4, showing the principal components and the construction.
Figure 4:
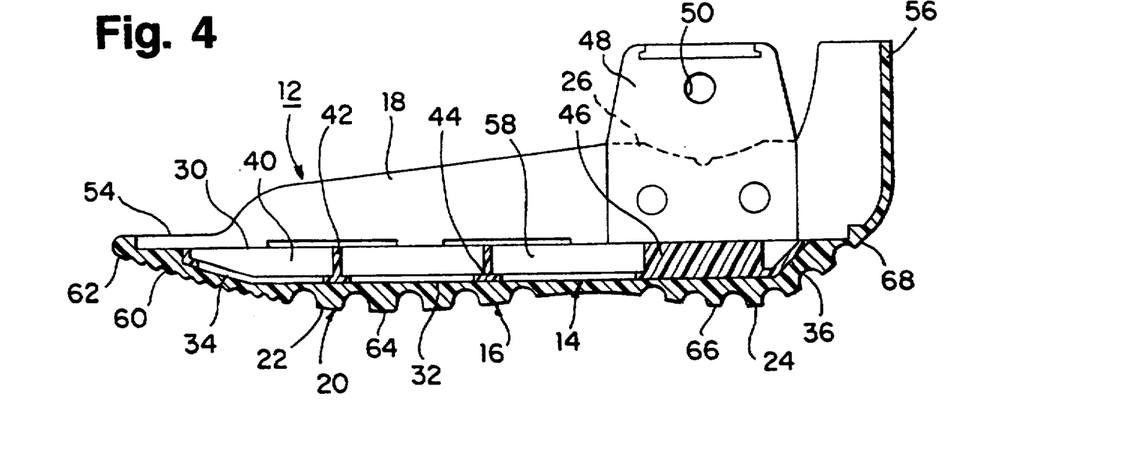
FIG. 4, is a vertical section of the moulded platform base through a line A–A1 in FIG. 3, showing the principal components, the construction and the profile of the sole.

With reference to FIGS. 3 and 4, which are sections, it may be seen that chassis 14, is a shallow structure, being generally a modified right-prism or parallelepiped, having top and bottom edges 30 and 32, respectively, which are substantially parallel except near the front, toe, region 34 and near the rear, heel, region 36, where in each case bottom edge 32, is angled upwards towards top edge 30. Chassis 14, is generally rectangular in plan, with side-walls 38 and 39, enclosing a plurality of longitudinal and transverse ribs, indicated generally at 40 and 42. Referring specifically to FIG. 4, it may be seen that the shape of ribs 40 and 42, resembles a narrow inverted 'T' section as indicated, for example, at 44. This substantially increases the strength of chassis 14. The resulting network or open grid of inverted 'T' sections does not interfere with the formation of over-mould 16 and is an important feature in integrating over-mould 16 and chassis 14, into a composite structure. The presence, disposition and section of ribs 40 and 42, are of importance to the way in which foot platform base 12 responds to the significant stresses which arise during ambulation.

Chassis 14, has few ribs in the rear, heel, region 36, which lies posterior to a perforated solid section 46, underlying the malleolar area. Extending upwards from perforated solid section 46, of chassis 14, are rigid upward extensions 48 and 49, exposed at 26 and 27, which have holes 50 and 51, respectively, shown in hidden detail in FIG. 3. Holes 50 and 51, provide receiving means described hereinbelow.

Over-mould 16, is resilient and substantially covers all of chassis 14, except the upper exposed portions 26 and 27, of rigid upward extensions 48 and 49. Over-mould 16, is generally designed to accommodate the human foot and is disposed symmetrically about the plan mid-line of chassis 14, in the form of a 'shoe' shape which is 'universal', being intended to fit both left and right feet using a compromise shape. Flexible upper 18, is formed by the upward extension of over-mould 16, commencing near the broadest point 52 and extending backwards around its periphery 54, increasing in height as it does so to reach a maximum behind the heel at 56. Downwards invaginations, indicated by way of example at 58, occupy the greater part but not all of the available upper space enclosed within each of the rectangular box sections formed by the disposition of longitudinal and transverse ribs 40 and 42, respectively, within chassis 14. Invaginations 58, are symmetrically and downwardly disposed within each space but do not perforate overmould 16.

Referring to FIG. 4, sole 20, is a downward extension of over-mould 16, which has a first, curved, rocker profile 22, which is accommodated by the upwards angled portion 34, of bottom edge 32, of chassis 14. First, curved, rocker profile 22, is provided with narrow transverse tread corrugations indicated at 60, near its front margin 62 and coarse transverse corrugations, indicated at their line of contact with the ground at 64, over the remainder of its surface. Sole 20, has a second, curved, rocker profile 24, which is accommodated by the upwards angled portion 36, of bottom edge 32, of chassis 14. Second curved rocker profile 24, is provided with coarse transverse corrugations, indicated at their line of contact with the ground at 66, substantially over all of its surface which extends to the rear margin 68, of sole 20. When foot platform base 12, is stood upon a level surface, the dispositions and thicknesses of first curved rocker profile 22 and second curved rocker profile 24, are such that foot platform base 12, presents a level support to a human foot placed upon it, which is bridged across coarse transverse corrugations at 64 and 66.

Figure 1:
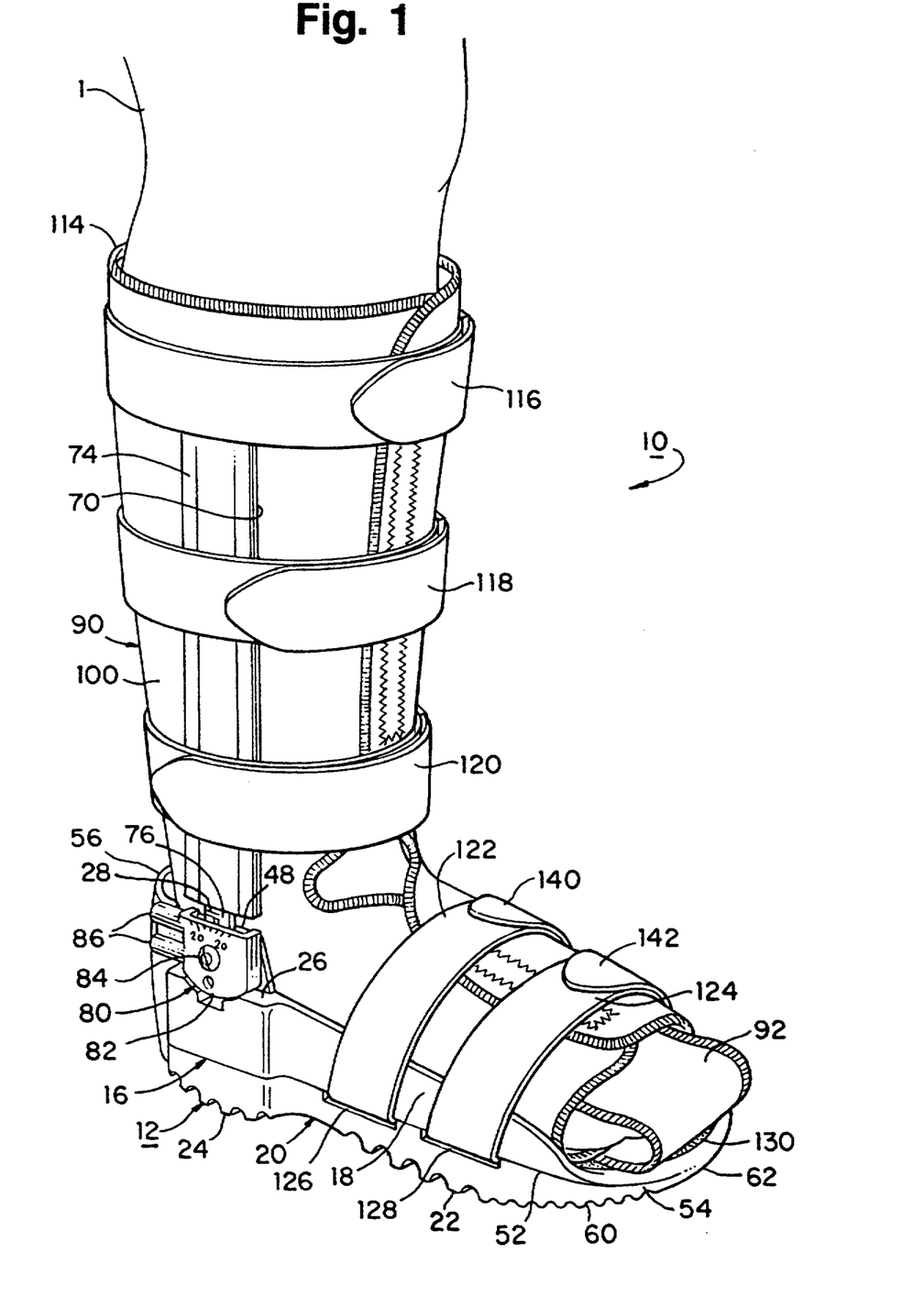
FIG. 1, is a general lateral perspective view of a hinged version of a lower leg walker according to the present invention with wrap components, straps and wraps placed as they would be, in use, on the foot ankle and lower leg of a patient.
Figure 2:
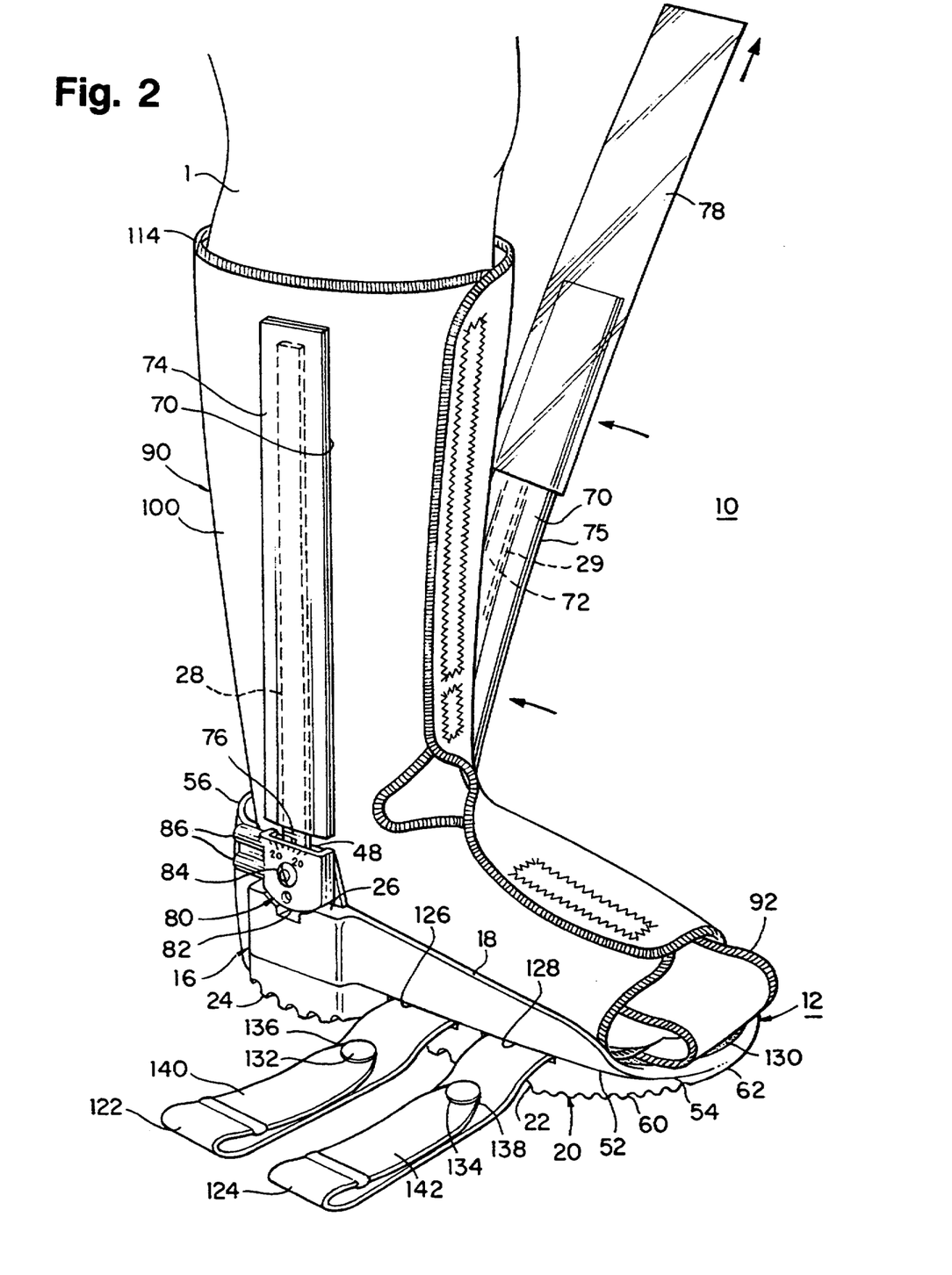
FIG. 2, is a lateral perspective view of the lower leg walker of FIG. 1, prior to the completion of fitting it to the foot, ankle and lower leg of a patient.

With reference now to FIGS. 1, 2, 5 and 6, it may be seen that, exposed regions 26 and 27, of rigid upwards extensions 48 and 49 of chassis 14, are attached to upright side-members 28 and 29. Strips of hook type fabric, such as commonly sold under the trademark Velcro ®, extend substantially over and somewhat beyond, the inner aspects of upright side-members 28 and 29. In FIG. 2, one hook strip 70, may be seen attached to inner aspect 72, of upright side arm 29 (not seen). Corresponding strips of loop type fabric 74 and 75, such as commonly sold under the trademark Velcro ®, extend similarly over the outer aspects 76 and 77, of upright side-members 28 and 29, respectively. On each side, the hook and loop fastening strips are secured to one another and to the upright side member by adhesive means, reinforced by sewing. A light gauge plastics slip-cover is provided for each pair of hook and loop type fabric strips as illustrated at 78, in FIG. 2.

Attachment means between the exposed portions 26 and 27, of rigid, upward, extension 48 and 49, of chassis 14, are in the form of hinging means 80 and 81. Hinging means 80 and 81, are each a single axis hinge arrangement for controlling plantar-flex and dorsi-flex motion at the ankle and comprise a hinge body, represented here at 82 and 83; a backplate, represented here by exposed regions 26 and 27, which are adapted to receive hinge bodies 82 and 83; a hinge arm, represented here by upright side-members 28 and 29, which are adapted for the purpose; pivotal securing means represented here at 84 and 85 and pairs of posteriorly directed adjustment means 86 and 87.

Figure 5:
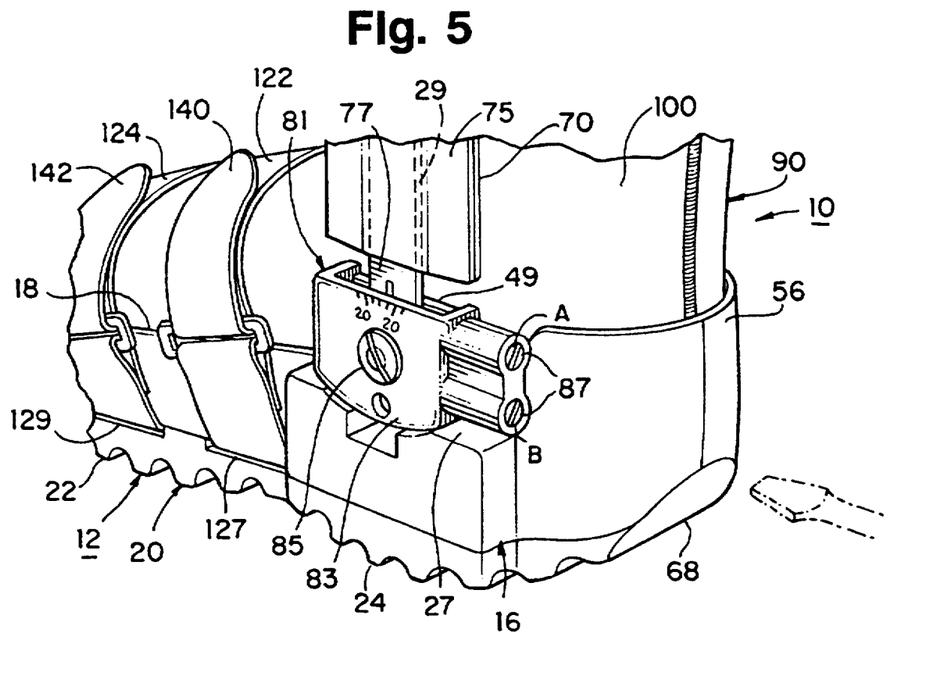
FIG. 5, is a rear, three-quarters, medial perspective view of part of the lower leg walker.
Figure 6:
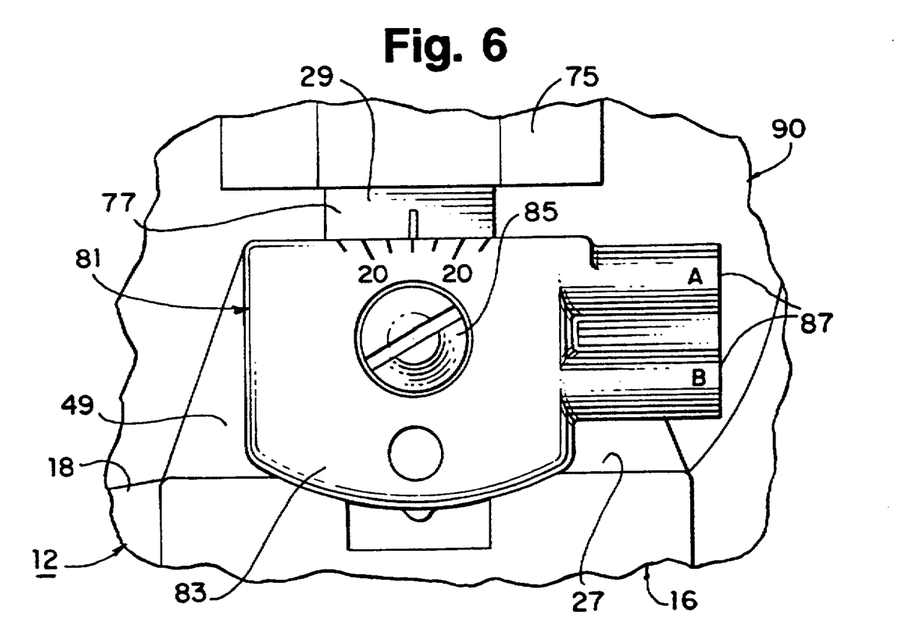
FIG. 6, is a side view of a hinge mechanism used in the first preferred embodiment.

In FIG. 5 and 6, there are shown representations of medial hinging means 81, in which the pair of posteriorly directed adjustment means 87, has the upper, dorsiflexion adjuster marked 'A' and the lower plantarflex adjuster marked 'B'. As indicated in FIG. 5, these are varied in their abutment positions by the use of a ¼" screwdriver to determine at what position between 22.5° of plantarflexion and 22.5° of dorsiflexion upright side member 29, will be arrested within hinge body 83.

Referring now to FIGS. 1, 2, 5, 7, 8 and 9, it may be seen that lower leg walker 10, is provided with a set of wraps and pads 88, comprising a main foot, leg and ankle wrap 90, a toe wrap 92, a heel pad 94 and ankle pads 96 and 97. All items comprising wrap and pad set 88, have the same construction. This is shown in a sectional detail in FIG. 9. The wrap materials comprise an open cell foamed plastics core 98, such as a polyether or polyurethane, having fabrics facings 100 and 102, bonded to the outside and inside, respectively. Facing 100, is fabric, such as brushed nylon, which is capable of secure attachment to hook closure fabric of the Velcro ® type. Facing 102, is placed towards the patient and is made of the towelling material well known as 'terry'.

Figures 7, 8:
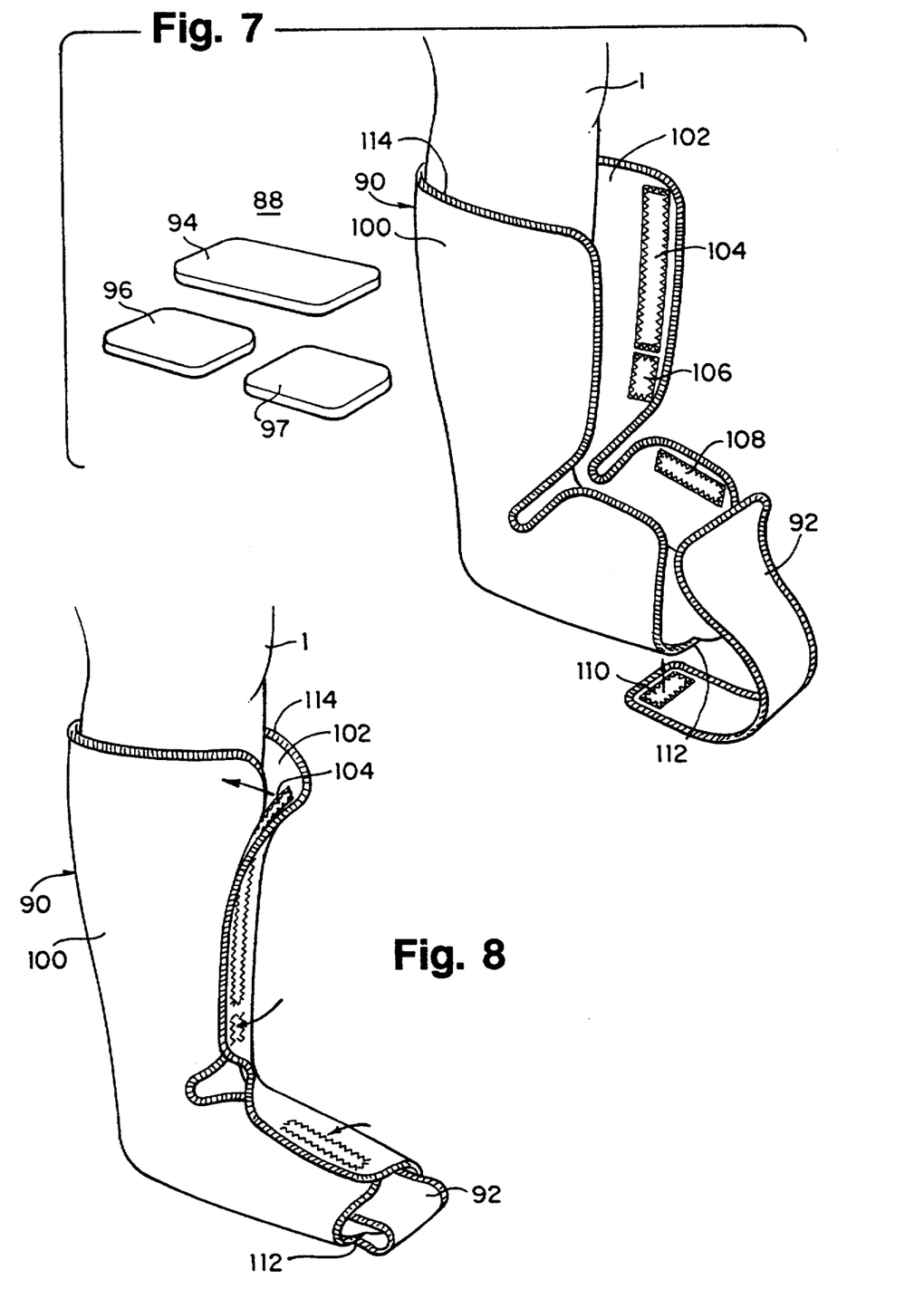
FIG. 7, is a perspective view of a wrap and pad set for the lower leg walker comprising a main wrap and toe wrap, together with the heel pad and ankle pads, together constituting a set.
FIG. 8, shows the main wrap and the toe wrap during fitting to the leg of the patient.

As may be seen by particular reference to FIG. 7, main wrap 90, has hook closure strips 104, 106 and 108, secured to its inner surface 102, to allow it to be closed upon itself, as shown in FIGS. 1, 2 and particularly 8, where the direction of closure is indicated by arrows. Toe wrap 92, has a short piece of hook closure strip 110, sewn to its inner surface so that it may be attached beneath the lower forward edge 112, of main wrap 90, as indicated in FIG. 7, by an arrow. In use, toe wrap 92, is folded back over the dorsum of the patient's foot and the main wrap 90, is closed firmly over it.

Lower leg walker 10, is an 'off-the-shelf' orthosis provided ready for use in a range of ready-made sizes. This means that there will inevitably be patients whom the device does not fit perfectly. Heel pad 94 and ankle pads 96 and 97, are used to improve the fit around the heel and the ankles, respectively. All wraps and pads are cut from sheet materials, preferably using a shaped die. Main wrap 90, has edges which are finished by piping or by the sewing method known as overlocking, as indicated at 114. Apart from toe wrap 92, the other wraps do not have finished edges so they may be easily trimmed, should this be necessary.

As hereinbefore described, light gauge plastics slip covers, as exemplified by 78, in FIG. 2, are provided for the Velcro ® type strips which extend over upright side-members 26 and 27. During the initial phase of fitting, the slip covers are left in place. When the patient's foot, ankle and lower leg 1, are enclosed in main wrap 90 and are being placed within lower leg walker 10, the slip covers prevent premature attachment of brush nylon facing 100, to Velcro ® type hook strips, exemplified by 70. Once main wrap 90, is accurately positioned, the covers may be drawn out from the top and discarded, precipitating immediate attachment of main wrap 90, to upright side-members 28 and 29. Alternatively, removal of the slip covers may be delayed until fitting and other adjustments are completed.

Turning to FIG. 1, it may be seen that broad straps 116, 118 and 120, secure the lower leg of a patient 1, enclosed in main wrap 90, within lower leg walker 10. Narrow straps 122 and 124, secure the foot and ankle. A pair of lateral longitudinal slots 126 and 128 and a pair of medial longitudinal slots 127 and 129, are provided within the periphery 54, of over-mould 16, at such a level that they will slidingly accommodate straps 122 and 124, just above top edge 30, of chassis 14 but below insole 130. Insole 130, is the surface upon which the patient's foot, within toe wrap 92 and main wrap 90, rests and constitutes the whole of the upper surface of foot platform base 12, within periphery 54, of over-mould 16. Insole 130, is made of closed cell polyethylene foam of the type known commercially as Plastazote ®.

In FIG. 2, straps 122 and 124, may be seen to be provided with small fabrics circles or dots 132 and 134, just inside the margins 136 and 138, of rounded tab ends 140 and 142.

The straps used in the preferred embodiment of lower leg walker 10, are all made from Velcro ® type hook and loop fabrics. All straps have loop rings at one end, a main length of loop closure material in the mid-section and a tab or closure length of hook closure material at the other end. The leg straps are broader, being conveniently made from 2" (50 mm) fabric, whilst the foot straps are conveniently 1½" (38 mm) wide.

Tab ends are rounded and each is provided with a small circle or dot of loop closure material which has a diameter about half that of the tab end, attached to the hook surface of the tab, just inside the margin. These enable the tabs to be opened easily, whilst ensuring that they remain closed during use. The dot can easily be removed if required.

Figures 9, 10:
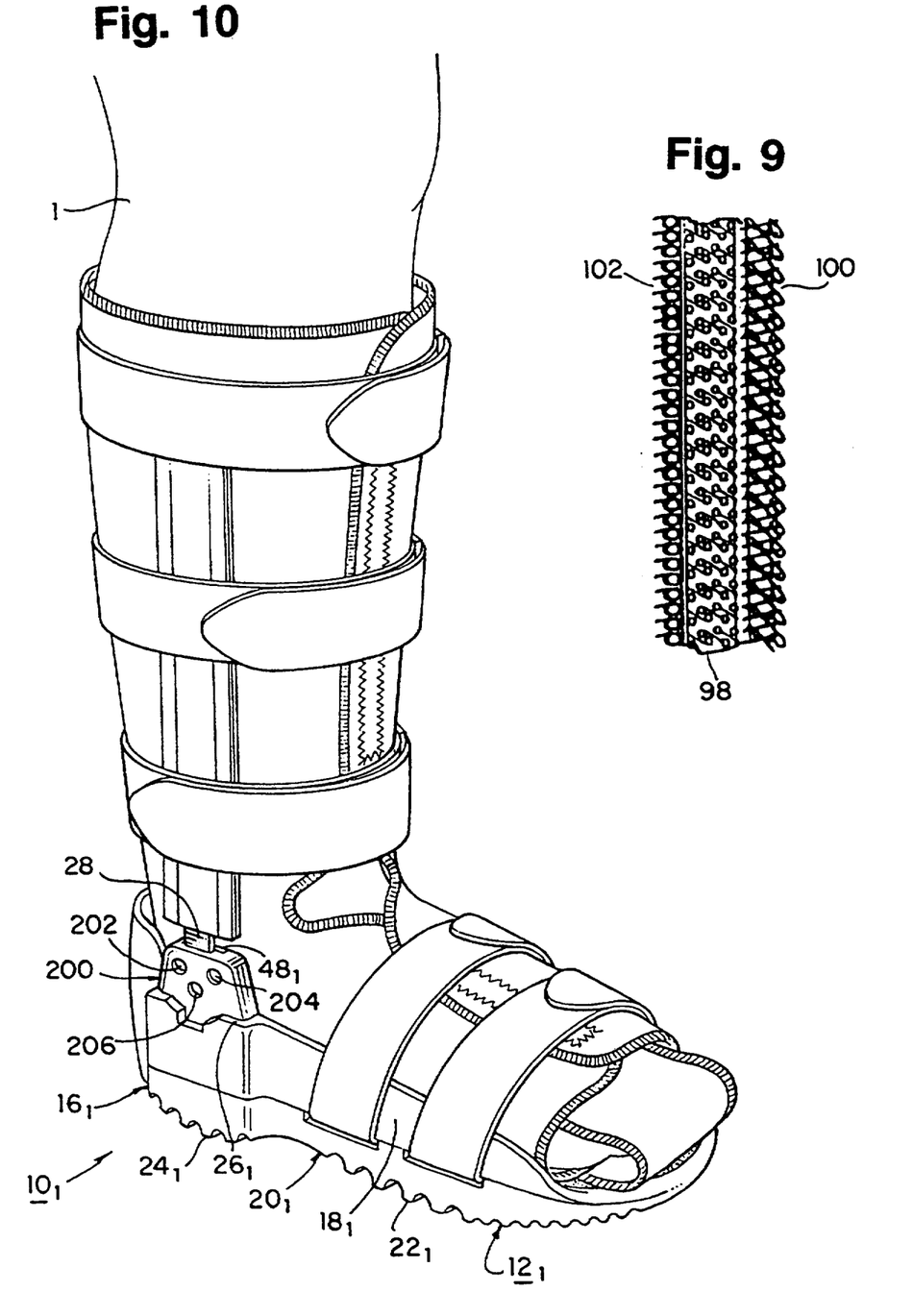
FIG. 9, shows a diagrammatic cross section detail of the wrap material.
FIG. 10, is a general lateral perspective side view of a fixed version of a lower leg walker according to the present invention with wrap components, straps and wraps placed as they would be in use, on the foot, ankle and lower leg of a patient.

Considering now a second most preferred embodiment, with reference to FIGS. 10 and 11, of the drawings, $10_1$, generally designates a lower leg walker that includes a foot platform base $12_1$, comprising a chassis, the main part of which is not seen in these drawings, substantially covered by an over-mould $16_1$, which is extended upwards into a flexible upper $18_1$, peripherally above and forming a sole $20_1$, below. Sole $20_1$, has a first rocker profile $22_1$, at the front end and a second rocker profile $24_1$, at the rear or heel end. The chassis has rigid upward extensions $48_1$, and $49_1$, in the malleolar area which are exposed at $26_1$ and $27_1$ and are adapted to receive upright side-members $28_1$ and $29_1$.

By brief comparison between FIGS. 10 and 11 and FIGS. 1 to 9, it will be seen that $10_1$, is substantially identical to lower leg walker 10, with the exception of the attachment between upright side-members 28 and 29 and foot platform base 12.

Returning to FIG. 10, it may be seen that in a lower leg walker $10_1$, upright side member $28_1$, is clamped against rigid upwards extension $48_1$, of chassis $14_1$, of foot platform $12_1$, by means of clamp 200. Clamp 200, rigid upwards extension $48_1$ and upright side member $28_1$, are correspondingly piercingly adapted to receive rivets 202, 204 and 206, which secure all three elements together.

Figure 11:
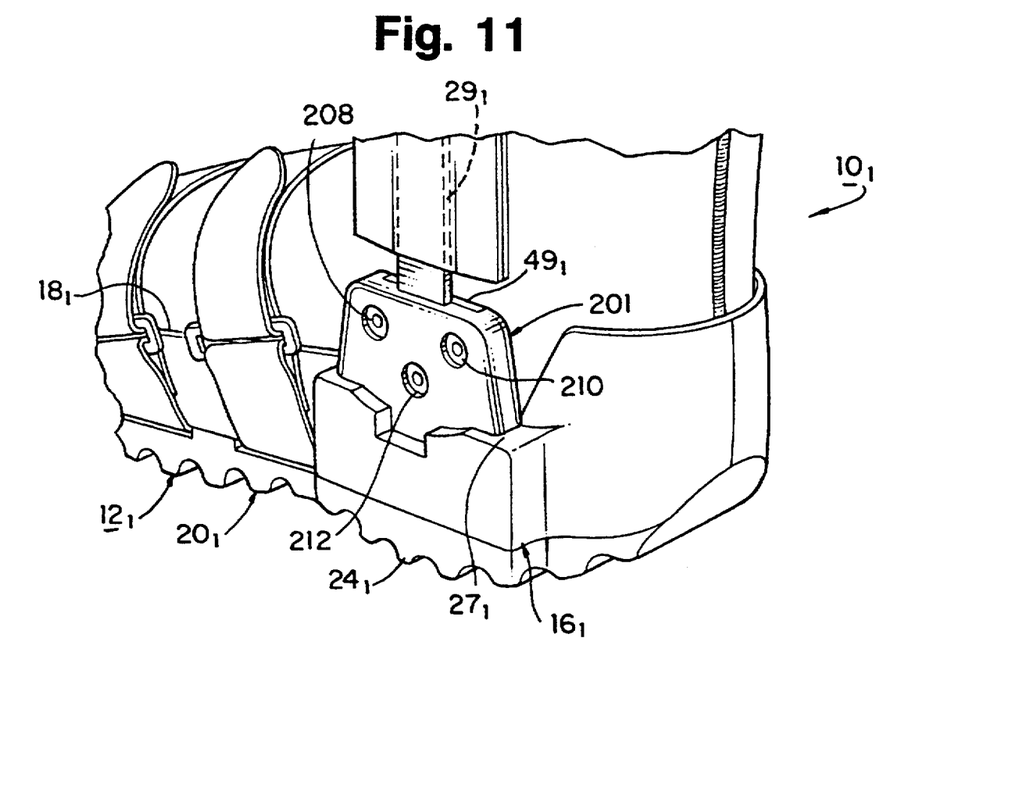
FIG. 11, is a medial side view showing attachment means between important components of the lower leg walker.

In FIG. 11, it may be seen that in a lower leg walker $10_1$, upright side member $29_1$, is clamped against rigid upwards extension $49_1$, of the chassis of foot platform $12_1$, by means of clamp 201. Clamp 201, rigid upwards extension $49_1$ and upright side member $29_1$, are correspondingly piercingly adapted to receive rivets 208, 210 and 212, which secure all three elements together.

Figure 12:
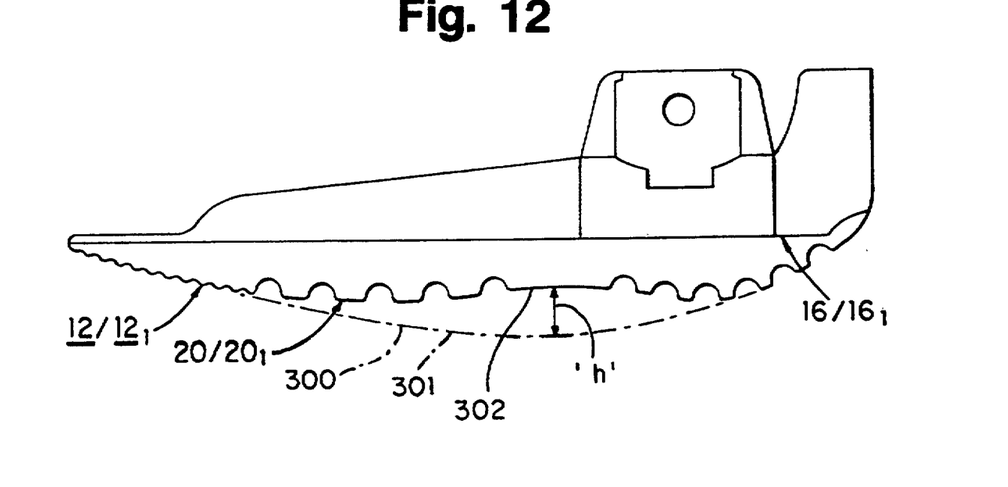
FIG. 12, is a diagrammatic side view of the composite foot platform base applicable to both most preferred embodiments of the present invention. The profile of a simple single rocker base is overlaid to show how the present invention saves height and mass when compared to prior art designs.

FIG. 12, shows a diagrammatic representation of foot platform base $12/12_1$ which is applicable to both most preferred embodiments 10 and $10_1$. Over-mould $16/16_1$, has a dual rocker profile of the type hereinbefore described. Overlaid diagrammatically, is the profile 300, of a simple continuous rocker design of the type used in prior art lower leg walkers indicated by a broken line. Dimension 'h' indicates the height reduction achieved by adopting the profile of the present invention and is a most important factor in reduced the energy costs of ambulation in the instant lower leg walker. The area between broken line 301, and the highest point 302, on the underside of sole $20/20_1$, indicates the cross sectional area of the over-mould material saved by adopting the profile of the present invention. This leads to significant weight savings which, although it has much less effect on the energy cost of walking in the instant device than is provided by the height saving, remains an important factor in patient acceptability.

The use of an insole covering an invaginated upper surface of a resilient over-mould on a rigid chassis in the most preferred embodiments provides an ideal combination of comfort, lightness and strength. The provision of adequate strength in lower leg walkers is very important and many prior art designs have been subject to frequent instances of failure. The compositing approach of the present invention allows the benefits of flexibility and resilience to be developed within the lower leg walker concept without any sacrifice of the rigidity or strength so important to a good outcome of treatment.

Consequently, walkers according to the invention are suitable for wider and more demanding applications in orthopaedic and rehabilitation medicine than prior art types.

What we claim is:

1. An ankle foot orthosis known as a lower leg walker and comprising:
    a foot platform base comprising;
    a substantially rigid chassis constructed as an open grid structure of the form of a modified right prism or parallelepiped having no entire upper or lower bounding wall and having side-walls which bound a first series of ribs disposed in a longitudinal manner and a second series of ribs disposed in a transverse manner and substantially enclosed within an over-mould formed in a resilient material to produce a shoe shape for supportively accommodating a human foot and incorporating an integral sole for contact with the ground, said sole being provided with a first longitudinally curved profile extending over the forward part of said integral sole and a second longitudinally curved profile extending over the rear part of said sole;
    said second longitudinally curved profile providing progressive rolling contact with the ground during that part of the ambulatory cycle of movement or gait cycle known as heel strike; and
    said first longitudinally curved profile providing rolling contact with the ground during that part of the ambulatory cycle of movement or gait cycle known as toe off;
    said sole thereby providing first and second zones of contact with the ground such that the upper surface of said foot platform base is substantially level when a human patient secured to it, stands still in that part of the ambulatory or gait cycle known as mid-stance; and
    attachment means for securing a pair of upright side-members disposed laterally and medially with respect to said foot platform base; and
    securing means for releasably securing said upright side-members to wrap means for enclosing a human foot, ankle and lower leg; and
    strap means for securing said orthosis to a human foot, ankle and lower leg.

2. Apparatus according to claim 1, wherein a chassis is formed in plastics.

3. Apparatus according to claim 1, wherein a chassis is formed in fibre reinforced resins.

4. The chassis of claims 1 to 3, wherein ribs have a cross-section which substantially resembles an inverted capital letter T.

5. The sole of claim 1, wherein first and second substantially longitudinally curved profiles are provided with transverse corrugations or grooves.

6. The apparatus of claims 1 to 3, wherein an over-mould formed in resilient materials is provided with a series of invaginations disposed symmetrically within and about segments defined by ribs.

7. Apparatus according to claims 1 to 3, wherein a resilient over-mould is shaped substantially like a shoe and is extended upwards around the periphery to form a side-wall or upper, said upper having a thin wall section relative to the body of said over-mould and extending from a point near the broadest part of said over-mould on a first side to a corresponding point on a second side, said upper being lowest at its points of origin and highest around the heel.

8. Apparatus according to claims 1 to 3, wherein are provided wrap and pad means for releasably enclosing the lower leg, foot and ankle of a Patient within a lower leg walker, all of said wraps and pads being cut from open cell foamed plastics sheets faced on the inside or skin-facing side, with terry material and on the outside with brushed nylon pile fabric material for releasably securing to releasable attachment means, secured non-releasably to the inward facing surfaces of upright side-members of the said lower leg walker.

9. Apparatus according to claim 8, wherein straps are provided with closure pieces at one end known as tabs, each tab being formed from hook closure fabric and being releasably affixed with a dot or circle of loop closure fabric, said dot or circle extending over a relatively small proportion of the total surface area of the tab rendering it easy to lift, whilst still retaining a full closing capability.

10. Apparatus according to claim 9, wherein attachment means between a foot platform base and medial and lateral upright side-members are each adapted to receive single pivot means constituting hinging means in the form of a hinge body provided with adjustment means comprising first posteriorly directed screw adjustment means above the pivot axis providing continuous variation of the limit of plantarflex travel and second posteriorly directed screw adjustment means below the pivot axis for continuous variation of the limit of dorsiflex travel said medial and lateral upright side-members each providing a first abutment stop above and to the rear of the pivot means and a second abutment stop to the rear and below the pivot means.

* * * * *